United States Patent [19]

Poncy et al.

[11] 4,051,849

[45] Oct. 4, 1977

[54] CATHETER FEEDING SYSTEM

[76] Inventors: Mark P. Poncy; Richard P. Poncy, both of 3660 E. Indus.Way, Riviera Beach, Fla. 33404

[21] Appl. No.: 674,162

[22] Filed: Apr. 6, 1976

[51] Int. Cl.² ............................................. A61M 5/00
[52] U.S. Cl. ............................... 128/214.4; 128/348; 128/DIG. 16
[58] Field of Search ............ 128/214.4, 221, 348–351, 128/DIG. 16

[56] References Cited

U.S. PATENT DOCUMENTS

| 1,120,549 | 12/1914 | Schellberg | 128/349 R |
|---|---|---|---|
| 3,154,080 | 10/1964 | Rowan et al. | 128/349 R |
| 3,185,151 | 5/1965 | Czorny | 128/214.4 |
| 3,757,771 | 9/1973 | Ruegg et al. | 128/214.4 |
| 3,894,540 | 7/1975 | Bonner | 128/214.4 X |

FOREIGN PATENT DOCUMENTS 1,534,119 6/1968 France ............................. 128/214.4

Primary Examiner—Dalton L. Truluck
Attorney, Agent, or Firm—Lane, Aitken, Dunner & Ziems

[57] ABSTRACT

In a catheter feeding system, a flexible resilient tube surrounds the catheter extending out of the catheter placement fixture. A portion of the tube is pleated adjacent to the fixture and the remainder of the tube is cylindrical. The catheter is fed forward by pinching the catheter through the tube between the thumb and forefinger behind the pleated portion and pushing the catheter forward into the fixture causing the tube to collapse axially in the pleated portion. A tubular jacket, which is also attached to the fixture, surrounds the pleated portion to keep it from wiggling out of axial alignment with the catheter during the feeding operation.

11 Claims, 7 Drawing Figures

CATHETER FEEDING SYSTEM

This invention relates to catheter feeding and more particularly to a method and apparatus for feeding a long catheter through a catheter placement fixture while maintaining sterility of the catheter.

In some medical procedures, such as, for example, sensing central veinous pressure, it is required for a long catheter to be inserted into a veinous or arterial system and feed a substantial length of the catheter through the blood vessel. The placement of the end of the catheter in the vein is achieved by means of a catheter placement apparatus, which is referred to as a fixture. The catheter fixture usually comprises a hollow needle which is used to make the initial puncture of the blood vessel into which it is desired to insert the catheter. With the needle point inserted through the wall of the blood vessel, the catheter is fed forward through the hollow needle and into the vein and then through the blood vessel a desired distance.

In such catheter placement and feeding systems, it is essential that the catheter remains sterile and free from contamination. In most systems now in use, the catheter is maintained sterile by means of a thin plastic film which is shaped into a sleeve or bag. The mouth of the bag is anchored to the rear of the placement fixture around the entrance of the placement fixture into which the catheter is fed when it is being guided by the needle of the apparatus into a blood vessel. The bag extends back from the catheter entrance of the placement fixture and completely covers the length of catheter trailing from the rear of the catheter placement fixture. In order to feed the catheter forward into the blood vessel of the patient, the person inserting the catheter grasps the catheter between his thumb and forefinger through the thin plastic film, which comprises the material of the bag, one to two inches to the rear of the catheter entrance of the placement fixture and the catheter is pushed forward in a short stroke. Then the catheter is released and regrasped again about one to two inches to the rear of the catheter entrance of the placement apparatus and the stroke is repeated. Typically, several strokes are required to feed the catheter to the desired position in the blood vessel. Only short strokes are used because if the catheter is grasped and pushed forward too far behind the catheter entrance of the placement apparatus the catheter would kink and retard forward motion. After a few forward strokes, a great deal of the thin plastic film comprising the bag material accumulates between the end of the catheter placement fixture and the point at which the catheter is grasped. Accordingly, after three or four strokes, the plastic bag must be pulled back because the accumulated bulk of the bag material will interfere with further advancing of the catheter. When the bag is pulled back, it often causes the catheter to be pulled back because the accumulated material of the bag will have collapsed around the catheter thus delaying successful completion of the procedure or even frustrating the entire purpose of the procedure.

In order to overcome this problem, a new catheter feeding device has recently been introduced in the form of a reel on which is wound the length of the catheter extending from the rear of the catheter placement apparatus. When the reel is cranked, it advances the catheter into and through the catheter placement apparatus. This approach is expensive and is disadvantageous because of the tremendous mechanical advantage that the reel provides to the user. This mechanical advantage results in a lack of control often causing kinking of the catheter. Moreover, the person performing the procedure is robbed of any feel for the threading operation, which feel is recognized as extremely important to achieve successful catheterization. The mechanical advantage provided by the reel readily overcomes the resistance of the interior of the blood vessel and may result in an injurious reaming action in the blood vessel.

The catheter advancing system of the present invention overcomes the problems of the prior art systems with extremely effective, yet simple, systems involving the use of pleated tubing to protecft the sterility of the catheter. Other proposals to solve the problem of catheter advancing while maintaining sterility have involved the use of pleated tubing to protect the sterility of the catheter, but these systems, which are relatively complex and appear likely to be inoperable or impractical, have not come into general use and have had little impact on the art.

BRIEF DESCRIPTION OF THE INVENTION

In accordance with the present invention, the catheter sterility is shielded by a tube made of sheet material which is flexible to bending stress, so that the catheter may be grasped through the tube by squashing the tube between the thumb and forefinger with little applied pinching force. Yet the sheet material of the tube must be sufficiently stiff and resilient so that the tube will spring back and retain its cylindrical shape when the pinching pressure is removed. The tube surrounds the catheter and fits into a receptacle around the catheter entrance to the catheter placement fixture. A short length of the tube adjacent to the fixture is pleated so that the tube will readily compress axially. In order to advance the catheter, the user grasps the catheter by pinching the tube behind the pleated portion and advancing the catheter into the fixture while axially compressing the pleated portion of the tube. To advance the catheter over a considerable distance, this action is repeated by releasing the catheter, re-extending the pleated portion of the tube, and repeating the forward stroke. To prevent the pleated portion from wiggling out of alignment and thus interfering with the forward advancement of the catheter, a second tube is provided slightly larger than the pleated portion of the first mentioned tube and positioned to surround this portion of the first mentioned tube.

The above described system provides an extremely simple, yet effective, system for advancing a catheter over a considerable length while maintaining the sterility of the catheter being advanced. Because the catheter is grasped by pinching it through the flexible tube, the user still maintains the necessary feel for successfully controlling the catheter feeding operation.

DESCRIPTION OF THE PREFERRED EMBODIMENTS

Figure 1:
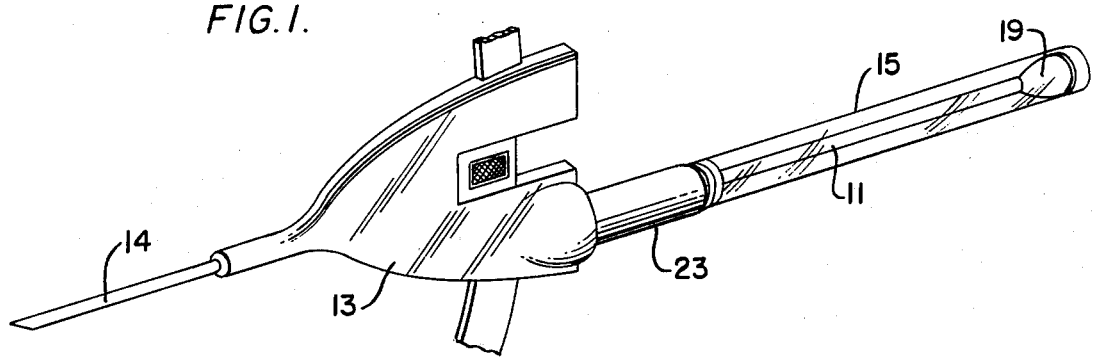
FIG. 1 is a perspective view of the catheter feeding system of the invention showing the catheter feeding mechanism attached to a catheter placement fixture.

In the embodiment of the invention illustrated in FIG. 1, the reference number 11 designates the catheter which is to be fed into a catheter insertion fixture 13 of the type disclosed in the copending application Ser. No. 595,014, invented by the inventors of this invention jointly with George W. Poncy. As described in that application, the fixture 13 comprises a hollow needle 14 which is used to puncture the blood vessel into which it is desired to insert the catheter. The catheter is then fed forward through the hollow needle 14 into the patient's blood vessel.

Figure 2:
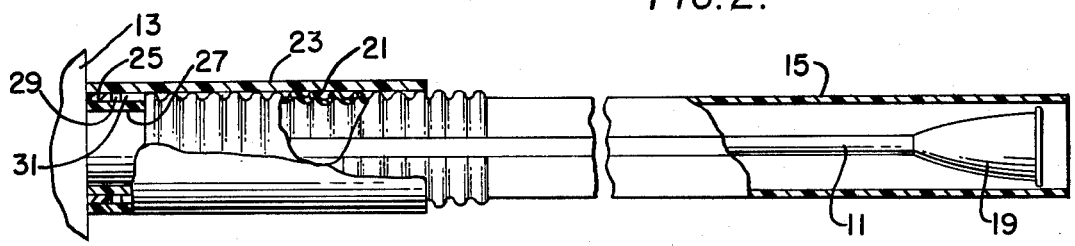
FIG. 2 is a view in elevation in partial section of the catheter feeding mechanism of the present invention.

As shown in FIG. 2, surrounding the catheter 11 is a transparent tube 15, which is about ⅜ inches in diameter and is attached to the catheter placement fixture 13 at the entrance into which the catheter 11 is to be fed.

The tube 15 is made long enough to extend beyond the back end of the catheter 11 where there is provided an adapter 19 for attaching the back end of the catheter to flexible tubing, referred to as I V tubing. A portion 21 of the flexible tube 15 adjacent to the fixture 13 is pleated with accordian pleats so that this portion of the tube may be axially compressed. The pleated portion should be 1 to 2 inches in length. The remainder of the tube 15 is cylindrical.

Figure 3:
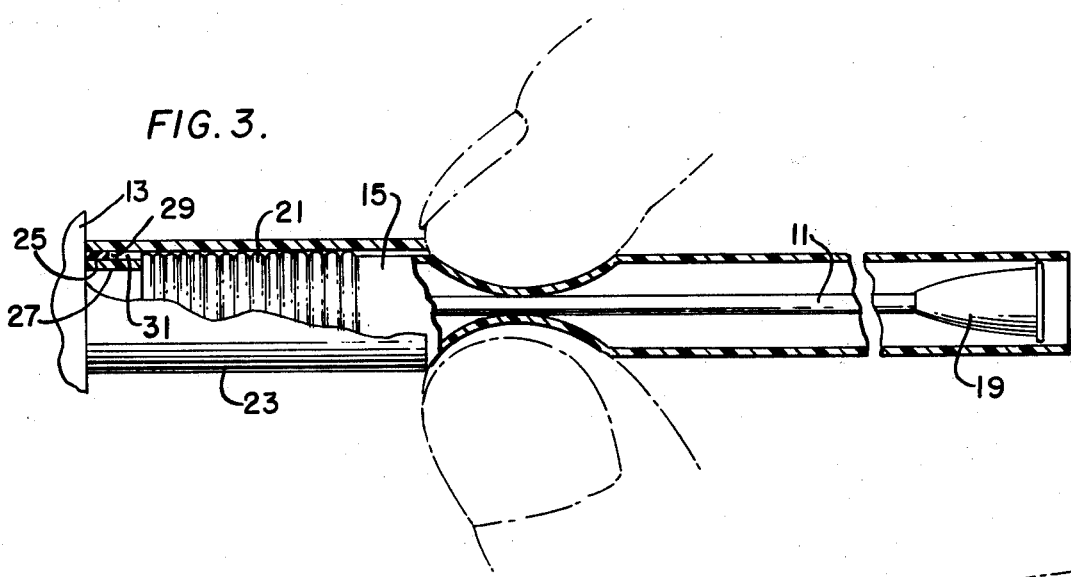
FIG. 3 is a view like that in FIG. 2 illustrating the feeding mechanism in operation.

In operation, the tube 15 is pinched between the thumb and forefinger in the cylindrical portion behind the pleated portion 21 so that the catheter 11 is grasped between the thumb and forefinger through the flexible tube 15. The catheter is then thrust forward a small distance into the catheter fixture 13 causing the pleated portion 21 to collapse axially as shown in FIG. 3. The catheter is then released allowing the natural resiliency of the tube 15 to cause the pleats 21 to expand axially back to its original expanded condition. If need be, the tube 15 can be axially pulled back to its original expanded condition if the natural resiliency of the pleats are not sufficient to bring the tube back to its original condition. This operation is then repeated as many times as desired to feed the catheter forward. In this manner, as much of the catheter as needed can be fed forward in repeated steps and a substantial length of catheter may be easily fed forward into the patient's blood vessel without any danger of contaminating the catheter. Moreover, the tube 15, which protects the sterility of the catheter does not interfere in any way with the feeding of the catheter 11.

As the pleated portion 21 is being axially collapsed, there is some tendency of the pleated portion of the tube 15 to move out of its cylindrical shape and form wiggles. Such wiggling is undesirable because it may result in the walls of the pleated portion 21 coming into contact with the catheter 11 and interfering with the catheter being fed forward through the fixture 13. To avoid this wiggling of the pleated portion 21, a tubular jacket 23 is provided surrounding the pleated portion 21 of the tube 15 and attached to the fixture 13 at the catheter entrance thereto. Preferably the jacket 23 does not extend the full length of the pleated portion 21 but extends to about ¼ inch from the end of the pleated portion. The tubular jacket 23 is provided with an inside diameter just larger than the outside diameter of the pleats of the portion 21 and may comprise a resilient flexible tube just like the unpleated portion of the tube 15.

After the catheter has been fed forward the desired distance, the tube 15 and jacket 23 may be pulled off of the fixture 13 and I V tubing may then be connected to the adapter 14. Alternatively, the I V tubing may be attached to the adapter 19 before the catheter 11 is fed forward so that the I V tubing is drawn into the tube 15 as the catheter is advanced. If this latter operation is not contemplated, the back end of the tube 15 may be closed to more perfectly protect the sterility of the catheter.

The tube 15 must be made of a material which is flexible to bending stress so that the cylindrical portion of the tube can be pinched between the thumb and forefinger with little effort to grasp the catheter 11 through the tube 15 as shown in FIG. 3 and a feel of the catheter through the tube 15 can be obtained. In addition, the tube 15 must be sufficiently resilient to spring back to its original shape when the pinching stress is removed. Moreover, the material of the tube should be sufficiently stiff so that the cylindrical unpleated portion of the tube not only will maintain its cylindrical shape in an unstressed condition but also will transmit the applied axial compressive stress to the pleated portion in the catheter advancing or feeding operation. The cylindrical portion of the tube 15 should transmit the compressive stress to the pleated portion 21 of the tube without being out of alignment with the cylindrical axis in the unpleated portion of the tube and the only axial compression should occur in the pleated portion. In order to achieve the above described properties, the material of the tube 15 should have a selected wall thickness which depends upon the material of the tube. Preferably the tube 15 is made of polypropylene in which case its wall thickness should be in the range of 4 to 14 mils. The optimum thickness for polypropylene is about 7 mils. Alternatively, polyethylene may be used for the tube in which case the optimum wall thickness for the material of the tube is 25 mils.

Figure 4:
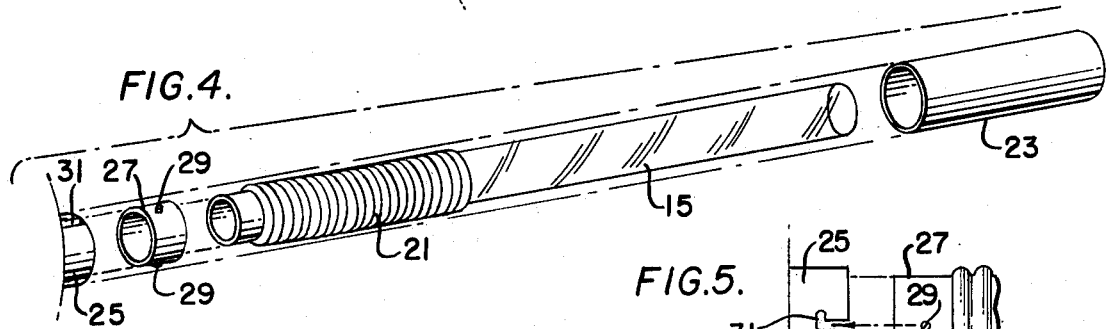
FIG. 4 is an exploded perspective view of the catheter feeding mechanism and its attachment to the catheter placement fixture.
Figure 5:
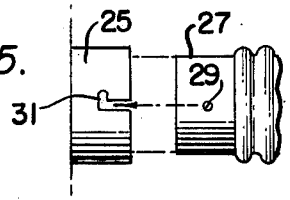
FIG. 5 is a view in elevation illustrating the details of the means by which the feeding mechanism is attached to the catheter fixture.

Attachment of the tube 15 and the tubular jacket 23 to the fixture 13 is illustrated in FIG. 4. As shown in this figure, the fixture 13 is provided with a cylindrical walled extension 25 about one-fourth of an inch in length surrounding and coaxial with the catheter entrance to the fixture 13. The front end of the tube 15, which attaches to the fixture 13, is positioned inside of the extension 25. This front end of the tube is made cylindrical and is provided with a molded piece 27 which fits over the cylindrical front end of the tube 15 and is glued thereto. The molded piece 27 is press-fit inside of the extension 25 and, as best shown in FIG. 5, is provided with pins 29 which fit into L-shaped slots 31 in the extension 25 to securely retain the assembly of tube 15 and the molded piece 27 on the extension 25 in axial alignment with the catheter entrance. The pleated portion 21 of the tube 15 starts at the outer end of the extension 25. The jacket 23 is press-fit over the extension 25. The pins 29 should be sufficiently short so that they do not protrude beyond the outer cylindrical wall of the extension 25 in order not to interfere with the press-fit of the jacket 23 on the extension 25. The press-fit of the molded piece 27 in the extension 25 and the jacket 23 over the extension 25 are made loose enough to permit the tube 15 and the jacket 23 to be removed and replaced without difficulty. Removal of the tube 15, as pointed out above, may take place after the catheter has been fed forward to the desired location in order to permit attachment of the I V tubing to the adapter 19. In addition, it may be desired to separate the jacket 23 from the pleated portion 21 in order to bend the tube 15 in the pleated portion 21 to provide a proper patient to bottle angle if the tube is left in place on the fixture.

Figure 6:
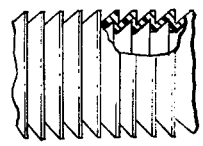
FIG. 6 illustrates an alternative type of pleating for the pleated portion of the catheter feeding apparatus.

The pleating of the tube 11 instead of being accordion pleating may comprise corrugations as shown in FIG. 6. The corrugations or corrugated pleating as illustrated in FIG. 6 is like that of the accordion pleating except that one-half of each pleat is reversed so that when the pleats are collapsed, each pleat will fit within its adjacent pleat. Moreover, when the pleats are axially collapsed, the pleats will hold themselves in a collapsed condition so that an axial tension is required to be applied to the tube to bring the corrugated pleating back to its extended condition. The nature of the corrugated pleating is such that any portion may be collapsed and held in a collapsed condition with one or more of the pleats fitting within the adjacent pleats and held in position with the remainder of the corrugated pleating in the axially extended condition. When this type of pleating is used, the user must axially draw the tube back to the original extended condition in order to feed the catheter forward in more than one stroke.

Figure 7:
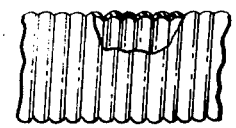
FIG. 7 illustrates another alternative pleating for the pleated portion of the tube catheter feeding apparatus.

Alternatively, the pleated portion may be in the form of convoluted pleating as shown in FIG. 7. In this type of pleating, the pleats are helical rather than each being circular as in the corrugated or accordian type pleating. As in the accordian pleating, there is significant tendency in this type of pleating to spring back to its original extended condition after the pleating has been collapsed.

In the catheter feeding device described above, the catheter is easily fed forward any desired amount while maintaining sterile protection of the catheter. Yet the tube 15 which maintains the protection of the catheter does not interfere in any way with the feeding forward of the catheter 11 and thus sterile feeding of the catheter is easily achieved.

Many modifications may be made to the above described embodiments of the invention without departing from the spirit and scope of the invention, which is defined in the appended claims.

We claim:

1. In a catheter placement and feeding system having a catheter fixture including a needle and a catheter having the front end thereof in said fixture and having the trailing end thereof extending out of said fixture from a catheter entrance in said fixture, said fixture adapted to guide said catheter along said needle when said catheter is fed forward into said catheter entrance, the improvement comprising: a tube for protecting the sterility of said catheter attached to said fixture at said catheter entrance surrounding the trailing portion of said catheter extending out of said catheter entrance, said tube having a flexible, resilient, cylindrical portion and a pleated portion, adapted to collapse axially, adjacent to said cylindrical portion and located between said cylindrical portion and said fixture, said cylindrical portion immediately adjacent to said pleated portion being sufficiently flexible to permit said catheter to be grasped through said cylindrical portion by pinching the cylindrical portion between the thumb and forefinger to collapse the wall of the cylindrical portion against the catheter and to provide a feel of the catheter through the wall of said cylindrical portion, said cylindrical portion being sufficiently resilient to return to its cylindrical shape after the pinching stress on the cylindrical portion has been removed.

2. A catheter placement and feeding system as recited in claim 1 wherein said tube is provided with a removable press-fit attachment to said fixture.

3. A catheter placement and feeding system as recited in claim 1 wherein said tube is a one-piece tube and wherein the space between said catheter and said tube throughout the length of said catheter from said cylindrical portion to said fixture is unobstructed.

4. A catheter placement and feeding system as recited in claim 1 wherein there is provided a second tube surrounding said pleated portion and having an inside diameter slightly greater than the outside diameter of said pleated portion.

5. A catheter placement and feeding system as recited in claim 4 wherein said second tube is attached to said fixture at said catheter entrance.

6. A catheter placement and feeding system as recited in claim 5 wherein both said first mentioned tube and said second tube are provided with removable press-fit attachments to said catheter fixture at said catheter entrance.

7. In a catheter placement feeding system having a catheter fixture including a needle and a catheter having its front end in said fixture and a trailing end extending out of said fixture from a catheter entrance in said fixture, said fixture being adapted to guide said catheter along said needle when said catheter is fed forward into said catheter entrance, the improvement comprising: a one-piece tube for protecting the sterility of said catheter attached to said catheter fixture at said catheter entrance surrounding the trailing portion of said catheter extending from said catheter entrance, said tube having a flexible, resilient, cylindrical portion and a pleated portion adapted to collapse axially between said cylindrical portion and said fixture, said cylindrical portion being sufficiently flexible to permit said catheter to be grasped through said cylindrical portion by pinching the cylindrical portion between the thumb and forefinger to collapse the wall of said cylindrical portion against said catheter and sufficiently resilient to return to its original shape after pinching stress on the cylindrical portion is removed, the space between said catheter and said tube throughout the length of said catheter from said cylindrical portion to said fixture being unobstructed.

8. In a catheter placement and feeding system having a catheter fixture including a needle and a catheter having the front end thereof in said fixture and having the trailing end thereof extending out of said fixture from a catheter entrance in said fixture, said fixture adapted to guide said catheter along said needle when said catheter is fed forward into said catheter entrance, the improvement comprising: a tube for protecting the sterility of said catheter attached to said fixture at said catheter entrance surrounding the trailing portion of said catheter extending out of said catheter entrance, said tube having a flexible, resilient, cylindrical portion and a pleated portion adapted to collapse axially between said cylindrical portion and said fixture, said cylindrical portion being sufficiently flexible to permit said catheter to be grasped through said cylindrical portion by pinching the cylindrical portion between the thumb and forefinger to collapse the walls of said cylindrical portion against the catheter, said cylindrical portion being sufficiently resilient to return to its cylindrical shape after the pinching stress on the cylindrical portion has been removed, and a second tube surrounding said pleated portion and having an inside diameter slightly larger than the outside diameter of said pleated portion.

9. A catheter placement and feeding system as recited in claim 8 wherein said second tube is attached to said fixture at said catheter entrance.

10. A catheter placement and feeding system as recited in claim 9 wherein both said first mentioned tube and said second tube are provided with removable press-fit attachments to said fixture.

11. A method of feeding a catheter through a catheter fixture while maintaining the sterility of said catheter, said fixture having a needle and being adapted to guide a catheter advanced into a catheter entrance of said fixture along said needle, comprising the steps of surrounding the trailing end of said catheter extending out of said catheter entrance with a tube having a flexible, resilient, cylindrical portion and a pleated portion between said cylindrical portion and said fixture, pinching said cylindrical portion to collapse the wall of said cylindrical portion against said catheter and grasp said catheter through said cylindrical portion, then while grasping said catheter through said cylindrical portion, pushing said catheter forward into said catheter entrance causing said pleated portion of said tube to collapse axially, then releasing the pinching stress on said cylindrical portion and returning said pleated portion to its axially extended condition, and then repeating said steps of pinching said cylindrical portion, pushing said catheter forward, releasing the pinching stress, and returning the pleated portion to its axially extended condition.

* * * * *